(12) United States Patent
Su et al.

(10) Patent No.: US 10,349,853 B2
(45) Date of Patent: Jul. 16, 2019

(54) MEDICAL ELECTRODE

(71) Applicant: KONINKLIJKE PHILIPS N.V., Eindhoven (NL)

(72) Inventors: Jie Su, Shangyu (CN); Ming Hong Fang, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 298 days.

(21) Appl. No.: 15/319,099

(22) PCT Filed: Jul. 2, 2015

(86) PCT No.: PCT/EP2015/065165
§ 371 (c)(1),
(2) Date: Dec. 15, 2016

(87) PCT Pub. No.: WO2016/001393
PCT Pub. Date: Jan. 7, 2016

(65) Prior Publication Data
US 2017/0127969 A1  May 11, 2017

(30) Foreign Application Priority Data

Jul. 3, 2014  (WO) ................ PCT/CN2014/081579
Sep. 3, 2014  (EP) .................................... 14183400

(51) Int. Cl.
*A61B 5/0408* (2006.01)
*A61B 5/0416* (2006.01)
(Continued)

(52) U.S. Cl.
CPC ........ *A61B 5/04087* (2013.01); *A61B 5/0416* (2013.01); *A61B 5/0448* (2013.01);
(Continued)

(58) Field of Classification Search
CPC .. A61B 5/0416; A61B 5/6833; A61B 5/68335
(Continued)

(56) References Cited

U.S. PATENT DOCUMENTS 1,938,231 A   12/1933  Ukropina
3,740,703 A   6/1973   Sessions
(Continued)

FOREIGN PATENT DOCUMENTS

EP  0194823 A2  9/1986
EP  0450350 A1  10/1991
(Continued)

*Primary Examiner* — Lee S Cohen

(57) ABSTRACT

The present invention provides a medical electrode, which comprises an annular adhesive pad (203) to be attached to a living being, a conductive pad (205) disposed in the central hole (207) of the annular adhesive pad, a first conductive snap element (209), a conductive element (211) and a sealing film (213). The conductive element (211) is configured to establish electrical communication between the conductive pad (205) and the first conductive snap element (209) and the sealing film (213) is attached to the annular adhesive pad (203) and to fix at least a portion of the conductive element (211) between the annular adhesive pad (203) and the sealing film (213). The flexibility and/or length of the conductive element is chosen to be large enough so as to allow the first conductive snap element (209) to move without causing the conductive pad (205) to move, resulting in reliable electrical contact between the conductive pad and the skin of the living being.

10 Claims, 3 Drawing Sheets

(51) Int. Cl.
   *A61B 5/0448* (2006.01)
   *A61B 5/0478* (2006.01)
   *A61B 5/0488* (2006.01)
   *A61B 5/05* (2006.01)
(52) U.S. Cl.
   CPC .......... *A61B 5/0478* (2013.01); *A61B 5/0488* (2013.01); *A61B 5/05* (2013.01); *A61B 2560/04* (2013.01); *A61B 2562/0209* (2013.01); *A61B 2562/164* (2013.01)
(58) Field of Classification Search
   USPC ........................................ 600/394, 391, 392
   See application file for complete search history.

(56) References Cited

U.S. PATENT DOCUMENTS

| | | | |
|---|---|---|---|
| 3,750,094 A | 7/1973 | Zenkich | |
| 3,977,392 A * | 8/1976 | Manley | A61B 5/0408 600/392 |
| 4,114,263 A | 9/1978 | Szpur | |
| 4,196,737 A | 4/1980 | Bevilacqua | |
| 4,370,984 A * | 2/1983 | Cartmell | A61B 5/04026 600/385 |
| 4,522,211 A * | 6/1985 | Bare | A61B 5/04087 439/325 |
| 4,934,383 A * | 6/1990 | Glumac | A61N 1/0456 607/152 |
| 2003/0078546 A1 | 4/2003 | Jensen | |
| 2003/0078646 A1 | 4/2003 | Axelgaard | |
| 2008/0132772 A1* | 6/2008 | Lang | A61B 5/0408 600/392 |
| 2010/0268113 A1 | 10/2010 | Bieberich | |

FOREIGN PATENT DOCUMENTS

| | | |
|---|---|---|
| RU | 2294135 C1 | 2/2007 |
| WO | 0205712 A1 | 1/2002 |
| WO | 2009098613 A1 | 8/2009 |
| WO | 2013164827 A2 | 11/2013 |

* cited by examiner

MEDICAL ELECTRODE

CROSS-REFERENCE TO PRIOR APPLICATIONS

This application is the U.S. National Phase application under 35 U.S.C. § 371 of International Application No. PCT/EP2015/065165, filed on Jul. 2, 2015, which claims the benefit of European Patent Application No. 14183400.2, filed on Sep. 3, 2014 and PCT/CN2014/081579, filed on Jul. 3, 2014. These applications are hereby incorporated by reference herein.

FIELD OF THE INVENTION

The invention relates to an electrode, in particular a medical electrode for establishing electrical contact with a living being to acquire physiological signals from said living being.

BACKGROUND OF THE INVENTION

In modern medicine, many medical apparatus are developed to acquire physiological signals from a living being by means of a medical electrode attached to the living being. For example, an ECG (electrocardiograph) device is widely used to acquire medical (i.e. biopotential) signals containing information indicative of electrical activity associated with the heart and pulmonary functions. An electrode is used to establish electrical connection between the ECG device and the skin of a living being, for example, a person or an animal and acquire physiological signals, which are one of the important bases for diagnosis of cardiovascular diseases or for monitoring cardiovascular and other physiological functions.

Stress Testing ECG is a diagnostic test performed on a person living with suspected or known cardiovascular disease, most commonly coronary artery disease (CAD). The stress testing procedure often requires the target person to exercise either on a treadmill or bike. Holter ECG is a diagnostic test performed on persons whose heart disease can only be detected through prolonged ECG monitoring or recording that normally takes 24 hours or even long. During Holter recording or monitoring, unavoidably, there would be frequent body movement of the person as a part of everyday life. To ensure quality of acquired ECG signals, both Stress ECG and Holter ECG require quality electrode to establish reliable electrical contact with the skin of the person.

FIG. 1 is an exploded perspective view of a conventional electrode used for an ECG device and FIG. 2 is a sectional view of the electrode of FIG. 1 when it is attached to the skin of a living being, for example, a person or an animal.

As shown in FIG. 1 and FIG. 2, an existing medical electrode 131 generally comprises an annular adhesive pad 133 having double-sided adhesive tape 147 and a central hole 137, a conductive pad 135 such as a foam pad filled with a conductive gel and disposed in the central hole 137 of the annular adhesive pad 133. The electrode 131 further comprises a first conductive snap element 139, a second conductive snap 141 and a sealing film 143 which is disposed between the first and second snap elements. The first conductive snap element 139 is to be attached to a first side 135a of the conductive pad 135, and be snapped into the second conductive snap 141. The outer portion of the sealing film 143 is attached to one side 133a of the annular adhesive pad 133.

The electrode may comprise a release liner 145, which is attached to a second side 133b of the annular adhesive pad 133 and can be removed before applying the electrode to a person. In use, the second conductive snap element 141 of the medical electrode 131 is snapped into a connector element C of a lead wire L, which transfers acquired signals to the ECG device.

Obviously exercising on a treadmill or bike, or body movements as part of everyday life may cause the lead wire L to move. When the lead wire L is fixed to the medical electrode, the mechanical force caused by the movement via the lead wire L will transferred from the first and second conductive snap elements and causes conductive pad 135 to move relative to the skin S of the living being, which in turn changes the electrical contact impedance between the conductive pad 135 and the skin S. This causes ECG signals distortion and introduces negative impact on ECG signal monitoring and diagnosis of relative disease.

To solve this problem, a known method is to use software algorithm to filter or correct the distortion or the interference after a noisy ECG waveform is acquired, but the software filtering may unexpectedly remove many ECG details due to lack of precise information of the movement causing such distortion. Thus, there is a need to provide an improved medical electrode for ECG devices, in particular, for Stress ECG and Holter ECG monitoring or diagnosis.

SUMMARY OF THE INVENTION

According to one aspect of the present invention, a medical electrode comprises an annular adhesive pad having a central hole and configured to be attached to a living being; a conductive pad disposed in the central hole of the annular pad and configured to be in direct contact with the living being; a first conductive snap element; a conductive element configured to establish electrical communication between the conductive pad and the first conductive snap element; and a sealing film configured to seal the conductive pad and to fix at least a portion of the conductive element between the annular adhesive pad and the sealing film, wherein the flexibility and/or length conductive element is chosen to be large enough so as to allow the first conductive snap element to move without causing the conductive pad to move. In this way, when the lead wire moves, the mechanical force transferred from the lead wire to the first conductive snap element will not cause relative movement between the conductive pad and the living being. As a result, the electrical contact impedance between the conductive pad and the living being will not change with body movement, thereby preventing the acquired physiological signals from being distorted.

More advantageously, the medical electrode further comprises a second conductive snap element into which the first conductive snap element is snapped; and a support sheet disposed between the first conductive snap element and the second conductive snap element. The support sheet comprises a central portion, an outer portion and an inner portion between the central portion and the outer portion. The central portion of the support sheet is sandwiched between the first and second conductive snap element, the outer portion of the support sheet is attached or adhered to the first side of the annular adhesive pad, and the inner portion of the support sheet is free from the annular adhesive pad and is designed in a way that allows at least a part of the inner portion of the support sheet to move relative to the outer portion of the support sheet.

Also more advantageously, the support sheet has one or more slits formed in the inner portion of the support sheet that enables the inner portion of the support sheet to deform when it is stressed with mechanical force transferred from lead wire via the second conduction snap element. This allows the inner portion of the support sheet to move relative to the outer portion of the support sheet with more freedom and without causing the outer portion of the support sheet and thus the annular adhesive pad to move and effectively increases reliability of the electrical contact between the conductive pad and the skin of the person when the body movement causes the lead wire to move.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
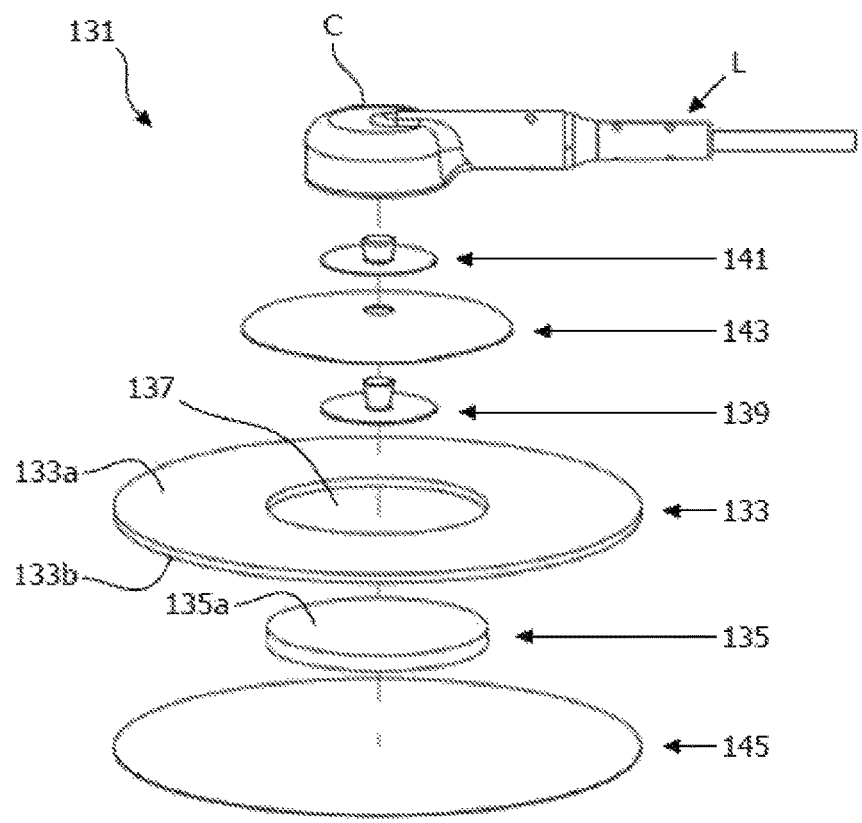
FIG. 1 is an exploded perspective view of a conventional medical electrode.
Figure 2:
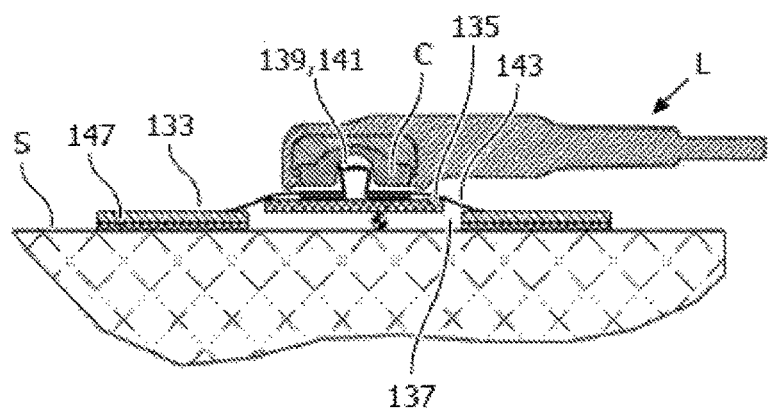
FIG. 2 is a sectional view of the medical electrode of FIG. 1 when attached to the skin of a living being.
Figure 3:
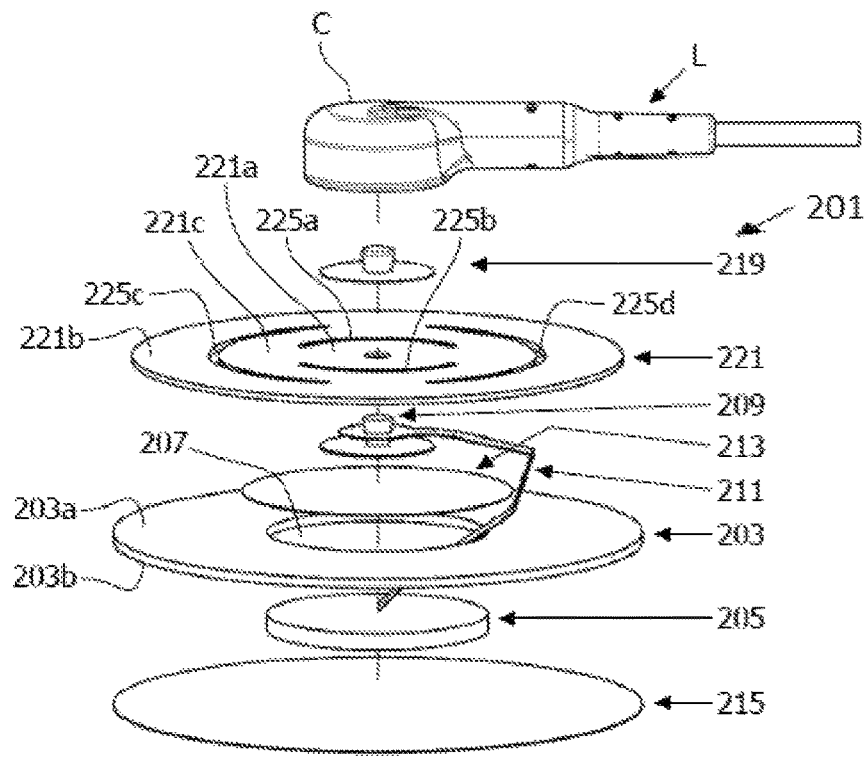
FIG. 3 is an exploded perspective view of a medical electrode according to an exemplary embodiment of the present invention.
Figure 4:
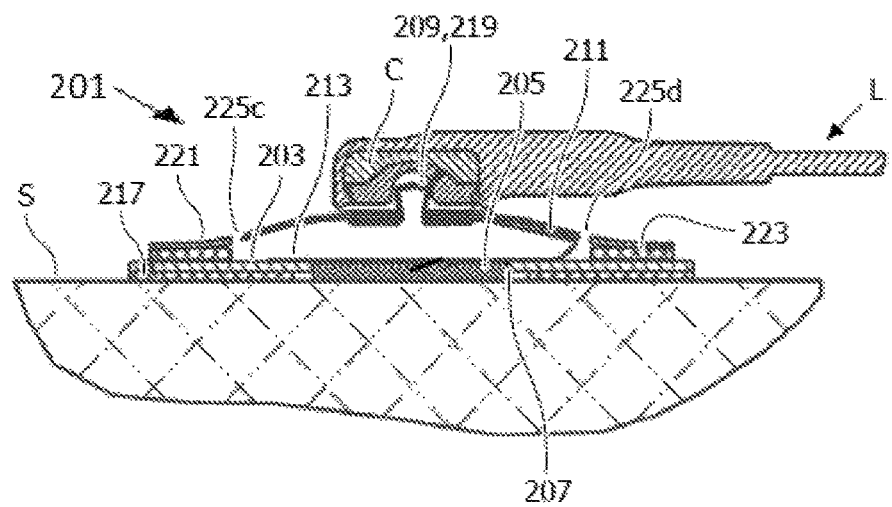
FIG. 4 is a sectional view of the medical electrode according to an exemplary embodiment of the present invention when attached to the skin of a living being.

As shown in FIGS. 3 and 4, a medical electrode 201 according to the present invention comprises an annular adhesive pad 203, a conductive pad 205, a first conductive snap element 209, a conductive element 211 and a sealing film 213.

The annular adhesive pad 203 has a central hole 207 and is to be attached to a living being such as a person or an animal. The conductive pad 205 is disposed in the central hole 207 of the annular adhesive pad 203 and to be in direct contact with the skin S of the person. Advantageously, the conductive pad 205 is a foam pad filled with conductive gel.

The first conductive snap element 209 is disposed adjacent to the sealing film 213. The conductive element 211 is configured to establish electrical connection between the conductive pad 205 and the first conductive snap element 209 and it can be a conductive foil or a strip with one end connected to the first conductive snap element 209 and the other end connected to the conductive pad 205.

The sealing film 213 is configured to be attached to a first side 203a of the annular adhesive pad 203 to prevent the conductive pad 205, in particular the conductive gel, from escaping from the central hole 207 of the annular adhesive pad 203. Meanwhile, the sealing film 213 also fixes at least a portion of the conductive element 211 between the annular adhesive pad 203 and the sealing film 213.

The medical electrode 201 may further comprises a release liner 215 configured to be attached to a second side 203b of the annular adhesive pad 203, for example, by means of a double-sided adhesive tape 217. The second side 203b of the annular adhesive pad 203 is opposite to the first side 203a of the annular adhesive pad 203 and is to be attached or adhered to the person when the medical electrode 201 is applied. In the state of use, the release liner 215 is removed, the annular adhesive pad 203 having double-sided adhesive tape 217 is adhered to the skin S of the person.

When the medical electrode 201 is used with an ECG device, the first conductive snap element 209 of the medical electrode is snapped into a connector element C of a lead wire L, which transfer acquired signals to the ECG device (not shown in the figures). The body movement of the person will cause lead wire L and thus the first conductive snap element to move. To protect the conductive pad from the mechanical force imposed on the first conductive snap element, the flexibility or the length of the conductive element 211 is designed to be large enough so as to absorb or accommodate the mechanical force and thus allow the first conductive snap element 209 to move without causing the conductive pad 205 to move. As a result, the electrical contact impedance between the conductive pad 205 and the skin S of the person will not change with movement of the lead wire L, and therefore, ensure stable and accurate ECG signals acquisition.

Advantageously, the medical electrode 201 according to the present invention further comprises a second conductive snap element 219 and a support sheet 221. The support sheet 221 is disposed between the first conductive snap element 209 and the second conductive snap element 219. Specifically, the support sheet 221 comprises a central portion 221a, an outer portion 221b and an inner portion 221c between the central portion 221a and the outer portion 221b. The central portion 221a of the support sheet 221 is sandwiched between the first conductive snap element 209 and the second conductive snap element 219, when the second conductive snap element 209 is snapped into the first conductive snap element 219. The outer portion 221b of the support sheet 221 is attached or adhered to the first side 203a of the annular adhesive pad 203 for example by means of a double-sided adhesive tape 223 while the inner portion 221c of the support sheet 221 is free from the first side 203a of the first pad 203. The inner portion 221c of the support sheet 221 is designed in a way that allow at least a part of the inner portion 221c of the support sheet 221 has freedom to move relative to the outer portion 221b of the support sheet 221 without causing the annular adhesive pad 203 to move.

As the sealing film and a part of the conductive element are sandwiched between the annular adhesive pad and the support sheet, it is possible to prevent the sealing film from becoming detached from the annular adhesive pad due to movement of the part of conductive element caused by the first snap element.

In one embodiment, the support sheet 221 is made from an elastic material, and the inner portion 221c and the outer portion 221b of the support sheet 221 can be made of different elastic material with different flexibility. Preferably the inner portion 221c of the support sheet 221 is more flexible than the outer portion 221b of the support sheet 221 to allow the inner portion 221c has freedom to move without causing the outer portion of the support sheet 221 to move.

Alternatively, the support sheet 221 may be made from a polymer material with more rigidity than a support sheet 221 made from elastic material. In such a case, to ensure that the inner portion 221c of the support sheet 221 has freedom to move relative to the outer portion 221b of the support sheet 221, a plurality of slits is formed in the inner portion 221c of the support sheet 221.

Figure 5:
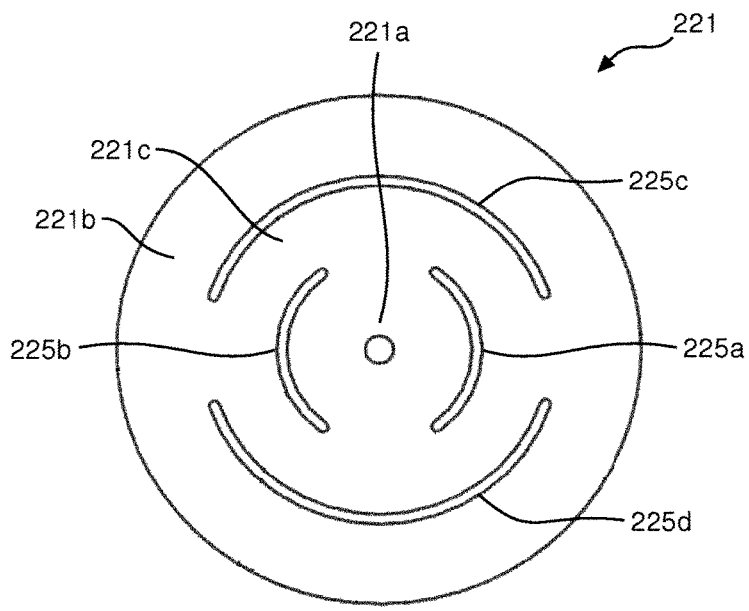
FIG. 5 is a top view of a support sheet of a medical electrode according to an exemplary embodiment of the present invention.
Figure 6:
FIG. 6 is a side view of the support sheet shown in FIG. 5.
Figure 7:
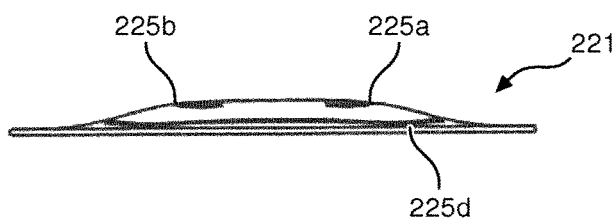
FIG. 7 is a schematic view showing a possible deformation of the support sheet shown in FIG. 6.

FIGS. 5, 6 and 7 show an exemplary support sheet 221. As shown in the FIGS. 5 and 6, a first pair of arc-shaped slits 225a, 225b is formed diametrically opposite each other in the inner portion 221c of the support sheet 221. Advantageously, a second pair of arc-shaped slits 225c, 225d with radius larger than that of the first pair of arc-shaped slits 225a, 225b may be formed diametrically opposite each other in the inner portion 221c of the support sheet 221. Preferably, the second pair of arc-shaped slits 225c, 225d are offset from the first pair of slits 225a, 225b by a certain angle, for example 85°-90°.

It should be understood that the number of slits is not limited to two pairs and more than two pairs of slits are also feasible. Further, the slits may be in any suitable shape, for example a linear or curved shape. For example, only one spiral slit may be formed in the inner portion 221c of the support sheet 221. Of course, more than one spiral slit is feasible. Since the inner portion 221c of the support sheet 221 has one or more slits, the inner portion 221c of the support sheet 221 is more flexible than the outer portion 221b of the support sheet 221. Thus, when the first and second conductive snap element is stressed due to movement of lead wire L, the inner portion 221c of the support sheet 221 may deform and thus move relative to the outer portion 221b of the support sheet 221. FIG. 7 shows such a possible deformation or movement of the inner portion 221c of the support sheet 221.

In use, the second conductive snap element 219 of the medical electrode is snapped into a connector element C of a lead wire L leading to the ECG device (not shown in the figures), the release liner 215 is removed and the medical electrode 201 is subsequently applied and attached to the skin S of the person by the double-sided adhesive tape 217, as shown in FIG. 5. When the lead wire moves due to the person's exercises on a treadmill or bike or by body movements, a mechanical force is generated that causes the first conductive snap element 209 and the second conductive snap element 219 to move. The flexibility or deformability of the inner portion 221c of the support sheet 221 allows the inner portion 221c of the support sheet 221 to move together with the first conductive snap element 209 and the second conductive snap element 219. As a result, the mechanical force generated by movement of the lead wire due to the person's exercises on a treadmill or bike or by body movements will not be transferred to the outer portion of the support sheet 221 and thus the annular adhesive pad 203. As the flexibility and/or length of the conductive element 211 is chosen to be large enough so as to allow a part of conductive element 211 to follow the inner portion 221c of the support sheet 221 Thus, a reliable electrical connection from the conductive pad 205 to the second conductive snap element 219 via the conductive element 211 and the first conductive snap element 209 is guaranteed. That is to say, irrespective of whether the lead wire moves perpendicularly to or along the skin S of the person, a mechanical force caused by the movement of the lead wire will not be transferred to the conductive pad 205. Thus, there is no relative movement between the second pad 205 and the skin S of the living being. As a result, the electrical contact impedance between the annular adhesive pad 205 and the skin S of the person will not change with the movement of lead wire. The stability and accuracy of ECG signals acquisition are improved.

Although the preferred embodiments of the present invention are interpreted as electrodes for an ECG device, it should be understood that the electrode according to the present invention may be used also with other medical devices, for example an EEG (electroencephalogram) device.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims.

What is claimed is:

1. A medical electrode comprising:
   an annular adhesive pad having a central hole and configured to be attached to a living being;
   a conductive pad disposed in the central hole of the annular adhesive pad;
   a first conductive snap element;
   a conductive element configured to establish electrical communication between the conductive pad and the first conductive snap element;
   a second conductive snap element into which the first conductive snap element is snapped;
   a support sheet disposed between the first conductive snap element and the second conductive snap element; and
   a sealing film configured to be attached to a first side of the annular adhesive pad and to fix at least a portion of the conductive element between the annular adhesive pad and the sealing film;
   wherein the conductive element is a flexible conductive foil and/or strip having one end electrically connected to the conductive pad and the other end electrically connected to the first conductive snap element and having flexibility and/or length large enough to allow the first conductive snap element to move without causing the conductive pad to move,
   and further wherein the support sheet comprises a central portion, an outer portion and an inner portion between the central portion and the outer portion, the central portion of the support sheet is sandwiched between the first conductive snap element and the second conductive snap element, the outer portion of the support sheet is adhered to the annular adhesive pad, the inner portion of the support sheet is free from the annular adhesive pad and designed in a way that allows at least a part of the inner portion of the support sheet to move relative to the outer portion of the support sheet without causing the conductive pad to move.

2. The medical electrode according to claim 1, wherein the support sheet is made from an elastic material.

3. The medical electrode according to claim 1, wherein the support sheet is made from two different materials such that the inner portion of the support sheet is more flexible than the outer portion of the support sheet.

4. The medical electrode according to claim 1, wherein the support sheet is made of a polymer material.

5. The medical electrode according to claim 1, wherein the support sheet has one or more slits formed in the inner portion of the support sheet.

6. The medical electrode according to claim 1 wherein the support sheet has a first pair of arc-shaped slits formed diametrically opposite each other in the inner portion of the support sheet.

7. The medical electrode according to claim 6, wherein the support sheet has a second pair of arc-shaped slits whose radius is larger than that of the first pair of arc-shaped slits formed diametrically opposite each other in the inner portion of the support sheet, the second pair of slits is offset from the first pair of slits by an angle.

8. The medical electrode according to claim 7, wherein the angle is between 85°-90°.

9. The medical electrode according to claim 1, wherein the conductive pad is a foam pad filled with conductive gel.

10. The medical electrode according to claim 1, wherein the medical electrode further comprises a release liner configured to be attached to one side of the annular adhesive pad that faces the living being when the medical electrode is applied and attached to the living being.

* * * * *